USO11795480B2

(12) United States Patent
Redford et al.

(10) Patent No.: US 11,795,480 B2
(45) Date of Patent: *Oct. 24, 2023

(54) HIGH PURITY STARCH STREAM METHODS AND SYSTEMS

(71) Applicant: POET Research, Inc., Sioux Falls, SD (US)

(72) Inventors: Steven Redford, Brandon, SD (US); Todd Peterson, Brandon, SD (US)

(73) Assignee: POET Research, Inc., Sioux Falls, SD (US)

( * ) Notice: Subject to any disclaimer, the term of this patent is extended or adjusted under 35 U.S.C. 154(b) by 321 days.

This patent is subject to a terminal disclaimer.

(21) Appl. No.: 17/009,456

(22) Filed: Sep. 1, 2020

(65) Prior Publication Data

US 2020/0399663 A1 Dec. 24, 2020

Related U.S. Application Data

(62) Division of application No. 14/983,320, filed on Dec. 29, 2015, now Pat. No. 10,793,879.

(60) Provisional application No. 62/098,654, filed on Dec. 31, 2014.

(51) Int. Cl.
| | |
|---|---|
| *C12P 7/06* | (2006.01) |
| *B02C 9/04* | (2006.01) |
| *B02C 23/14* | (2006.01) |
| *B02C 13/22* | (2006.01) |
| *C12P 7/10* | (2006.01) |

(52) U.S. Cl.
CPC ........ *C12P 7/06* (2013.01); *B02C 9/04* (2013.01); *B02C 13/22* (2013.01); *B02C 23/14* (2013.01); *C12P 7/10* (2013.01)

(58) Field of Classification Search
CPC ............................................. C12P 7/00–625
See application file for complete search history.

(56) References Cited

U.S. PATENT DOCUMENTS

| | | | |
|---|---|---|---|
| 3,979,375 A | 9/1976 | Rao et al. | |
| 4,287,304 A * | 9/1981 | Muller | C12P 19/14 426/11 |
| 7,138,257 B2 | 11/2006 | Galli et al. | |
| 7,303,899 B2 | 12/2007 | Baldwin et al. | |
| 7,452,425 B1 * | 11/2008 | Langhauser | B02B 5/02 127/38 |
| 9,777,303 B2 | 10/2017 | Jakel et al. | |
| 10,233,466 B2 * | 3/2019 | Redford | C12P 7/06 |
| 10,480,038 B2 | 11/2019 | Jakel et al. | |
| 10,793,879 B2 * | 10/2020 | Redford | C12P 7/06 |
| 11,060,116 B2 | 7/2021 | Redford | |
| 2004/0023349 A1 * | 2/2004 | Bisgaard-Frantzen | C12P 7/10 435/161 |
| 2004/0187863 A1 | 9/2004 | Langhauser | |
| 2006/0251762 A1 | 11/2006 | Jansen et al. | |
| 2007/0259410 A1 * | 11/2007 | Donaldson | C12N 9/0006 435/254.2 |
| 2010/0059609 A1 * | 3/2010 | Teeter, Jr. | B02C 9/04 241/11 |
| 2013/0337517 A1 | 12/2013 | Razavi-Shirazi et al. | |
| 2014/0106419 A1 | 4/2014 | Bazzana et al. | |
| 2016/0186215 A1 | 6/2016 | Redford | |
| 2016/0201091 A1 | 7/2016 | Redford et al. | |
| 2016/0222135 A1 | 8/2016 | Lee | |
| 2018/0016602 A1 | 1/2018 | Franko et al. | |
| 2019/0284593 A1 | 9/2019 | Jakel et al. | |
| 2019/0284649 A1 | 9/2019 | Jakel et al. | |
| 2019/0309377 A1 | 10/2019 | Jakel et al. | |
| 2021/0163996 A1 | 6/2021 | Redford | |

FOREIGN PATENT DOCUMENTS

| | | | | |
|---|---|---|---|---|
| WO | WO-2006119386 A2 * | 11/2006 | | C12P 7/06 |
| WO | 2009015333 A1 | 1/2009 | | |
| WO | 2013180863 A1 | 12/2013 | | |
| WO | 2014100685 A1 | 6/2014 | | |

OTHER PUBLICATIONS

Unpublished Utility U.S. Appl. No. 17/365,027, filed Jul. 1, 2021.
International Search Report and Written Opinion from International Application No. PCT/US2015/067944, dated Apr. 15, 2016 (12 pages).
Kwiatkowski et al. "Modeling the process and costs of fuel ethanol production by the corn dry-grind process" Industrial Drops and Products, vol. 23, pp. 288-296, 2006, (9 pages).
Jakel, "Product Diversification: Proven Path Forward", Presented at American Coalition for Ethanol Annual Conference, Omaha, NE, Aug. 2017, https://ethanol.org/news/news/2017/08, (71 pages).
Robert, "Industrial Glucose: Bridging the Biochemical GAP", Presented at ABLC2019, Renewable Chemicals Summit, Washington, DC, Apr. 4, 2019, (20 pages).
International Search Report and Written Opinion from International Application No. PCT/US2015/067951, dated Apr. 20, 2016 (11 pages).
Jessen, "The Quest for Maximu Yield: Wet Mill to Dry Mill", Ethanol Producer Magazine, Aug. 15, 2011, pp. 1-2, (2 pages).

(Continued)

*Primary Examiner* — Thane Underdahl
(74) *Attorney, Agent, or Firm* — Kagan Binder, PLLC

(57) ABSTRACT

Methods and systems for isolating a high purity starch stream are provided. The methods provide an initial treatment step in advance of traditional grinding or fractionation operations (such as dry milling or wet milling operations) that facilitate separation of starch from other components of starch-based grains, for example facilitate separation of soft endosperm from other components of corn kernels including hard endosperm. The systems include a first treatment system for separating a high purity starch stream from other components of the grain stream, wherein the system can be configured as a bolt on for traditional milling operations such as wet milling and dry milling operations.

20 Claims, 2 Drawing Sheets

(56) References Cited

OTHER PUBLICATIONS

Mueller et al., "2012 Corn Ethanol: Emerging Plant Energy and Environmental Technologies", University of Illinois at Chicago, Energy Resources Center, College of Engineering, Apr. 29, 2013, pp. 1-31, (31 pages).
Wang et al., "Effect of Endosperm Hardness on an Ethanol Process Using a Granular Starch Hydrolyzing Enzyme", Transactions of the the Asabe, vol. 53, No. 1, Jan. 1, 2010, pp. 307-312, (6 pages).
Ezeji et al., "Production of acetone-butanol-ethanol (ABE) in a continuous flow bioreactor using degermed corn and Clostridium beijerinckii", Process Biochemistry, vol. 42, pp. 34-39, 2007, (6 pages).
Taylor et al., "Dry-Grind Process for Fuel Ethanol by Continuous Fermentation and Stripping", Biotechnol. Prag. vol. 16, pp. 541-547, 2000, (7 pages).
Dien et al., "The U.S. corn ethanol industry: An overview of current technology and future prospects", Int. Sugar Jnl., vol. 104, No. 1241, 2002, (8 pages).
Kim et al., "Composition of corn dry-grind ethanol by-products: DOGS, wet cake, and thin stillage", Bioresource Technology, vol. 99, pp. 5165-5176, 2008, (12 pages).
Sigma Aldrich Chemicals—Technical Library "Particle Size Conversion Table" accessed at https://www.sigmaaldrich.com/chemistry/stockroom-reagents/learning-center/tech n ical-1 i brary/particle-Size-conversion. html available on 2009, (1 page).

* cited by examiner

HIGH PURITY STARCH STREAM METHODS AND SYSTEMS

CROSS-REFERENCE TO RELATED APPLICATIONS

This application is a divisional Patent Application of nonprovisional patent application Ser. No. 14/983,320, filed Dec. 29, 2015, titled HIGH PURITY STARCH STREAM METHODS AND SYSTEMS, which claims the benefit of U.S. Provisional Application No. 62/098,654, entitled, "HIGH PURITY STARCH STREAM METHODS AND SYSTEMS", and having a filing date of Dec. 31, 2014, wherein the entireties of each of the nonprovisional application and the provisional applications are incorporated by reference.

FIELD

The specification generally relates to methods and systems for producing a slip stream of starch, such as a high purity slip stream of starch, in ethanol fermentation facilities. The specification also relates in part to methods and systems for producing a slip stream of starch, for example for the production of non-ethanol chemicals, in ethanol fermentation facilities with little to no impact on the ethanol facility's alcohol yield. This specification also relates in part to methods and systems for improving the economics of corn-to-ethanol fermentation processes.

BACKGROUND

The demand for renewable fuels and chemicals has been growing significantly over the last years to reduce reliance on petroleum. At the same time, interest in biofuels, such as ethanol, as an alternative to petroleum has greatly increased, in part due to the desire to promote domestic rural economics. Ethanol is the most commonly used biofuel, and current U.S. biofuel is almost exclusively derived from corn. However, economics is an obstacle to widespread adoption of biofuels.

Conventional ethanol fermentation facilities produce ethanol from starch-based feedstock such as corn. In a typical conventional corn-to-ethanol fermentation process, starch present in corn is broken down into simple sugars, which can be fermented by an ethanologen such as yeast into ethanol. An approach that has been taken to improve the economic viability of starch-based corn ethanol production is to make other components of corn available to sell. More specifically, some conventional processes use a wet mill rather than dry mill corn-to-ethanol approach.

In dry milling, whole kernels of corn are ground to produce a single stream of whole ground corn for the corn ethanol conversion process. By contrast, in wet milling, corn is steeped—soaked in water to soften the grain and facilitate separating the various components of the corn kernel—to produce separate streams of starch, fiber and germ. Whereas the starch stream is used in the corn ethanol conversion process, the fiber and germ streams may be separately processed into other products.

While wet milling processes provide a cleaner separation between endosperm, bran, and germ as compared to dry milling processes, it is a very capital intensive process that requires numerous pieces of equipment in order to produce a high purity starch stream. On the other hand, while dry milling processes are considerably less expensive than comparable capacity wet milling processes, dry milling processes do not provide the stream purity that may be desirable for some downstream processes. Whole corn grinding creates a corn flour from the entire corn kernel that is too comingled with bran and germ to allow separation of a high starch stream.

SUMMARY

The present disclosure relates in part to methods and systems for producing both a starch stream for the production of non-ethanol chemicals ("bio-chemicals") as well as a starch stream for the production of ethanol in ethanol fermentation facilities while maintaining a commercially-acceptable ethanol titer. In some embodiments, the dual bio-chemical and ethanol starch streams are produced while essentially maintaining the same ethanol titer as could be produced by the same facility if it did not produce the bio-chemical starch stream. In some embodiments, the present disclosure provides methods and systems for producing a starch stream, for example a high purity starch stream, in the context of any of the above-mentioned milling scenarios, and which can be installed as initial method steps or system components in those milling scenarios.

In some embodiments, methods according to this disclosure comprise producing from a starch-based stream such as a corn stream, a first high-starch stream comprising at least about 88% starch on a dry basis and a second feedstock stream which is suitable for further processing in a dry mill or wet mill (such as a corn dry mill or corn wet mill) operation. In some embodiments, the high-starch stream comprises at least about 90% starch on a dry basis. In some embodiments, the high-starch stream comprises at least about 94% starch on a dry basis. In some embodiments, producing comprises processing corn kernels in a manner that facilitates separating at least a portion of the starch from the remaining stream based on size. In some embodiments, the size of the at least portion of the starch is about 500 microns or less. In some embodiments, the size of the at least portion of the starch is about 260 microns or less.

In some embodiments, methods according to this disclosure comprise producing from a corn stream a first high-starch stream comprising soft endosperm and at least about 88% starch on a dry basis and a second feedstock stream comprising hard endosperm and which is suitable for further processing in a corn dry mill or wet mill operation; the producing step comprises processing corn kernels in the corn stream to facilitate separation of at least a portion of the soft endosperm from the corn stream. In some embodiments, the high-starch stream comprises at least about 90% starch on a dry basis. In some embodiments, the high-starch stream comprises at least about 94% starch on a dry basis.

In some embodiments, processing results in at least a portion of the soft endosperm having a sufficiently small enough size that it can be separated from the corn stream by its size. In some embodiments, the size is about 500 microns or less. In some embodiments, the size is about 260 microns or less.

In some embodiments, the process further involves producing ethanol from the feedstock stream in a starch-based (e.g. corn) fermentation process. In some embodiments, in order to compensate for removal of starch (such as soft endosperm) from the feedstock stream, producing ethanol involves using a higher grind rate than a similar conventional starch-based (for example corn) fermentation process using grain-based starch feedstock (e.g. whole corn kernels) would use. In further embodiments, the process involves removing at least a portion of the additional non-starch components present as a result of the increased grind rate to achieve a ratio of fermentable to non-fermentable components that is sufficiently equivalent to a similar conventional starch-based (e.g. corn) fermentation process using grain-based starch feedstock (e.g. whole corn kernels) to maintain ethanol production at the level of the similar starch-based (e.g. corn) fermentation process.

In some embodiments, the disclosure provides a starch-based grain-to-ethanol fermentation system comprising a dry mill or wet mill ethanol fermentation system which produces beer from feedstock sugars derived from a feedstock stream; and, a bolt-on pretreatment system configured to produce a first starch stream for producing feedstock sugars and a second, high purity starch stream, both of which are derived from the feedstock stream. In some embodiments, the high purity starch stream comprises at least about 88%, or at least about 90%, or at least about 94% starch on a dry weight basis. In some embodiments, the bolt-on pretreatment system is configured to facilitate separation of starch in the feedstock stream into a feedstock starch stream and a high starch stream based on size.

In some embodiments, the starch-based grain-to-ethanol fermentation system is a corn-to-ethanol fermentation system comprising a dry mill or wet mill ethanol fermentation system which produces beer from feedstock sugars derived from a feedstock stream comprising hard endosperm; and, a bolt-on pretreatment system configured to produce the hard endosperm feedstock stream and a high purity starch stream derived from soft endosperm, wherein the high purity starch stream comprises at least about 88%, or at least about 90%, or at least about 94% starch on a dry weight basis. In some embodiments, the bolt-on pretreatment system is configured to mill the initial feedstock in a manner that facilitates separating hard endosperm stream from soft endosperm based on size.

In further embodiments, one or more bio-chemicals are produced from the high-starch stream. In other embodiments, ethanol is produced from the feedstock stream. In some embodiments, the high-starch stream comprises up to about 50% of the soft endosperm in the corn kernels.

The identified embodiments are exemplary only and are therefore non-limiting. The details of one or more non-limiting embodiments according to the disclosure are set forth in the accompanying drawings and the descriptions below. Other embodiments according to the disclosure should be apparent to those of ordinary skill in the art after consideration of the present disclosure.

DETAILED DESCRIPTION

Figure 1:
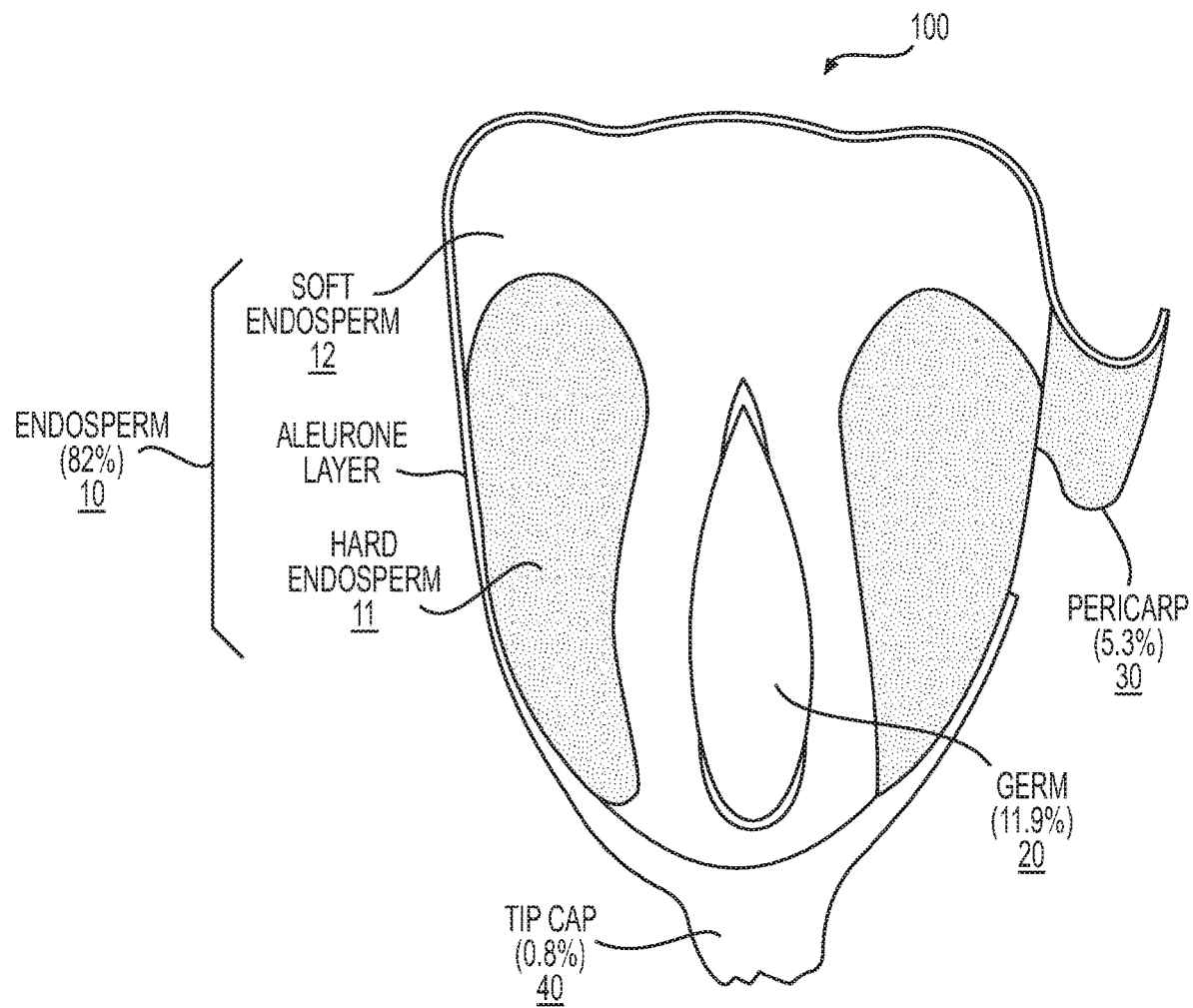
FIG. 1 is a schematic illustration of the components of a corn kernel.

Unless defined otherwise, all technical and scientific terms used herein have the same meaning as is commonly understood by one of ordinary skill in the art to which this disclosure belongs. In the event that there is a plurality of definitions for a term herein, those in this section prevail unless stated otherwise.

Wherever the phrases "for example," "such as," "including" and the like are used herein, the phrase "and without limitation" is understood to follow unless explicitly stated otherwise.

The terms "comprising" and "including" and "involving" (and similarly "comprises" and "includes" and "involves") are used interchangeably and mean the same thing. Specifically, each of the terms is defined consistent with the common United States patent law definition of "comprising" and is therefore interpreted to be an open term meaning "at least the following" and also interpreted not to exclude additional features, limitations, aspects, etc.

The term "about" is meant to account for variations due to experimental error or to permit deviations from the measurements that don't negatively impact the intended purpose. All measurements or numbers are implicitly understood to be modified by the word about, even if the measurement or number is not explicitly modified by the word about.

The term "substantially" is meant to permit deviations from the descriptive term that don't negatively impact the intended purpose. All descriptive terms are implicitly understood to be modified by the word substantially, even if the descriptive term is not explicitly modified by the word substantially.

Where ever the terms "a" or "an" are used, "one or more" is understood unless explicitly stated otherwise or such interpretation is nonsensical in context.

Where ever the text refers to extracting, separating, purifying or the like, it is understood that the action may not result in a complete extraction, separation or purification. Likewise, the term "purify" and the like does not mean 100% pure but rather only that the target product is not part of the same original mixture in which it is found. Thus for example, the phrase "separating soft endosperm from the remaining components of the corn" and the like means "separating at least a portion of the soft endosperm" even where "at least a portion" is not explicitly stated. Accordingly, "the remaining components of the corn" includes the portion of soft endosperm that was not removed.

The term "bio-chemical" means a non-ethanol chemical made from sugar derived from feedstock that can be used in a feedstock-to-ethanol (such as corn-to-ethanol) production process.

The phrase "high starch" or "high purity starch" or the like means at least 88% starch on a dry weight basis. In some embodiments, the high purity starch has a starch content of at least 90% on a dry weight basis. In some embodiments, the high purity starch has a starch content of at least 94% on a dry weight basis.

The term "producing" or the like means "producing directly or indirectly" unless explicitly stated otherwise or nonsensical in context. For example, "producing a bio-chemical from starch" includes producing the bio-chemical in a multi-step process wherein starch would be the feedstock and there may be one or more intermediate steps prior to producing the desired bio-chemical.

Conventional ethanol production processes typically involve five basic steps: milling, cooking, saccharification, fermentation, distillation and recovery. In some such processes, the milling step is a dry milling step in which corn is ground into flour producing a whole ground corn feed stream. In other such processes, the milling step is a wet milling step in which corn is soaked in water producing a starch feed stream for corn ethanol conversion and separate germ and fiber streams for independent processing. Cooking may involve mixing the feed stream (e.g. flour) with water to form a slurry, heating the slurry to above the gelatinization temperature of the corn, and treating the slurry with a liquefying enzyme to hydrolyze starch contained therein to dextrins. In the saccharification step, enzymes are added to the mash to convert the corn starch into simple sugars. The fermentation of the sugars by an ethanologen such as yeast produces a beer, which is separated into ethanol and whole stillage by distillation. The whole stillage may be subject to further processing wherein it is separated into wet cake and thin stillage. The thin stillage passes through evaporators to produce a syrup, which may be recombined and dried with the wet cake to produce distillers grains with soluble (DDGS), an animal feed. Not all non-starch-based ethanol production processes involve all the identified steps. For example, in some such processes, saccharification and fermentation are not independent steps but occur simultaneously. As another example, some processes do not involve a cooking step.

A co-pending application entitled "Economic Ethanol Fermentation Sugar Stream, Process and Systems of Producing Same" by Steven Redford and assigned to POET Research, Inc. relates to production of a slip stream of sugar, for example for the production of bio-chemicals, and is primarily directed at feedstock-to-ethanol fermentation processes that involve separate saccharification and fermentation steps (although in some embodiments, the approach may be implemented in simultaneous saccharification and fermentation ("SSF") processes). The methods and systems described herein relate to production of a slip stream of starch (which can be further processed into sugar and bio-chemicals) and is primarily directed at starch-based feedstock-to-ethanol fermentation processes (such as corn-to-ethanol processes) that involve SSF, although here again the approach is more broadly applicable, including to processes involving separate saccharification and fermentation steps.

In some embodiments, the present disclosure relates to methods and systems for producing a slip stream of starch, such as a high purity slip stream of starch, in the context of starch-based grain (for example corn) milling operations, which may further be a part of a starch-based grain ethanol (e.g. corn ethanol) and/or bio-products facility. In some embodiments, the methods and systems according to the present disclosure may be "bolted on" to (attached to) existing starch-based grain-to-ethanol (such as corn-to-ethanol) fermentation processes and facilities as preliminary process steps or system components. For example, the methods and systems may be bolted on to existing corn-to-ethanol fermentation processes and facilities in advance of the existing (dry or wet) mill processes or components. Because the slip stream of starch is produced in advance of saccharification and fermentation (in fact the starch stream may be produced in advance of conventional starch-based grain-to-ethanol (e.g. corn-to-ethanol) milling operations), the methods and systems according to this disclosure may be implemented in ethanol facilities in which saccharification and fermentation are performed either simultaneously or independently.

In some embodiments, the starch slip stream may be further processed into sugar, on-site or off-site (or partly on-site and partly off-site). In some further embodiments, the resultant sugar may be used as feedstock for production of one or more bio-chemicals (also on site or offsite or combinations thereof).

Referring now to the figures, wherein like reference numerals indicate like elements, as shown in FIG. 1, a corn kernel 100 comprises endosperm 10, germ 20, pericarp 30 and a tip cap 40. Also as shown, the endosperm 10 component of the corn kernel comprises about 82% of the kernel by weight and is made up of both hard 11 and soft endosperm 12. The present disclosure provides methods and systems for producing a first portion of starch having a sufficiently different average size from remaining components of the grain (including a sufficiently different average size from a second portion of starch) to facilitate removing the first portion of starch from remaining components using size separation techniques. In some embodiments, the present disclosure provides methods and systems that target and exploit the difference in the soft and hard endosperm for deriving a slip stream of starch, for example in the context of corn milling and/or corn fermentation processes. In some embodiments, the present disclosure provides methods and systems for reaching a high purity starch stream. The disclosure provides methods and systems that may isolate a high purity starch stream.

Figure 2:
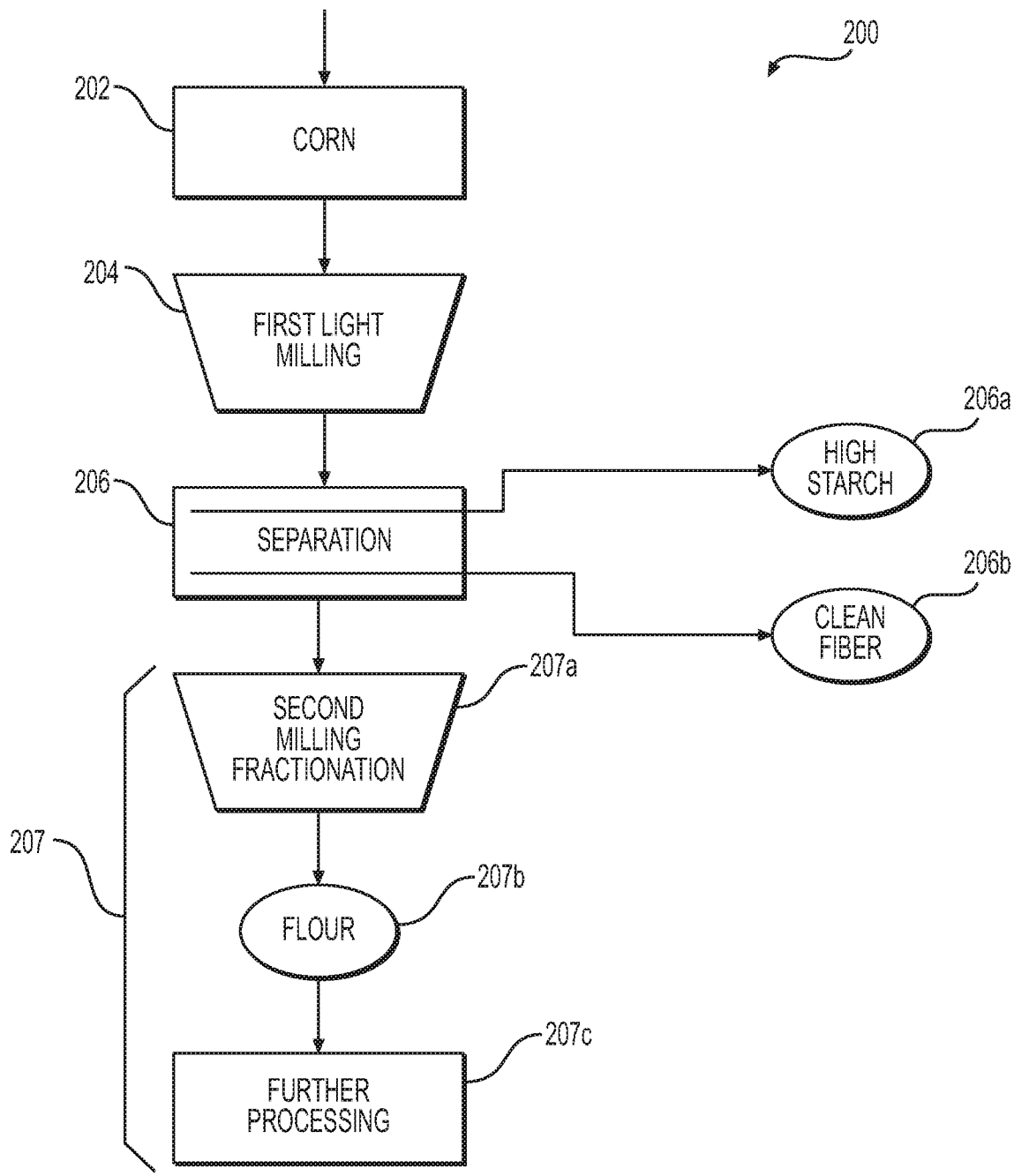
FIG. 2 is a process flow diagram of an embodiment of a method according to this disclosure.

FIG. 2 is a process flow diagram illustrating an embodiment of a method for isolating a high purity starch stream in accordance with this disclosure. As shown in FIG. 2, the method 200 begins at the start block 202, wherein whole shelled corn is introduced for processing. In some embodiments, the corn may first be cleaned and possibly moisture adjusted using traditional tempering and drying techniques, for example to improve bran coat removal. In some embodiments, the corn may also be temperature adjusted using traditional means.

At block 204, the grain is subjected to an initial treatment configured to produce a treated stream, which facilitates separation of at least a portion of the starch from the remaining components of the corn. In the illustrated embodiment, the kernels are subjected to an initial treatment configured to produce a treated stream, which facilitates separation of at least a portion of the endosperm from other components of the kernel. In some embodiments, the treatment is configured to produce a treated stream, which facilitates separating soft endosperm from the remainder of the stream (from hard endosperm and other components of the corn).

In some such embodiments, the treatment is a milling procedure which results in reducing at least a portion of the soft endosperm to a size that is sufficiently smaller than the remaining components in the treated stream such that the portion may be separated from the rest of the treated stream by size. For example, in some embodiments, the treatment may be a light milling procedure resulting in a treated (or in this case "milled" stream), which light milling procedure is targeted to reduce up to 50% of the soft endosperm in the incoming corn stream to a fine flour which could be separated from the rest of the milled stream by size. In some such embodiments a pin mill may be used to cause the soft endosperm, for example up to 50% of the soft endosperm, to crumble into a fine flour having a particle size of about 500 microns or less.

After the initial treatment step 204, the treated stream is sent to a first separation step 206, which separates at least a portion of the starch in the incoming treated stream from the remaining components of the treated stream. In embodiments wherein the separated starch is derived from soft endosperm, such as the above-described light milling procedure, the separated starch stream is a high starch stream comprising at least 88% starch on a dry basis. In some embodiments, the initial treatment step, such as the initial impact or grinding step, produces a high purity starch stream comprising at least about 90% starch on a dry basis. In some embodiments, the high purity starch stream comprises at least about 94% starch on a dry basis. As a person of skill should understand, the purity of the separated starch is dependent on how commingled the starch is with non-starch components. In some embodiments, the purity level of the starch is inversely related to the amount of starch removed; when smaller quantities are removed, purity levels of 94% or greater can be achieved with higher quantities of starch removal driving down the purity. In some embodiments, the slip stream of starch, such as the high purity slip stream of starch, may be further refined to enhance the starch percentage.

In some embodiments, the first separation step 206 is a multi-step process wherein a high starch stream is separated from the main ground corn steam ("treated" stream or "milled" stream) in one sub-step 206a, and one or more other non-starch components are separated out in one or more additional sub-steps. In the illustrated embodiment, fiber is separated out from the main ground corn stream in a separate sub-step 206b. In either case, because the first treatment 204 is configured to facilitate separation of endosperm from other components of the kernel, in some embodiments, typical separation techniques can be used to remove the high purity starch stream. For example, where a pin mill has been used resulting in the soft endosperm crumbling into a fine particle size (or "dust") relative other components of the stream, typical size separation techniques may be used to remove the portion of soft endosperm in the form of a high purity starch dust from the rest of the stream.

As a more specific example of the initial treatment step 204 and separation step 206 the initial treatment 204 may involve grinding the corn through a pin mill such as a Sturtevant Model 6A Pin Mill. The pin mill may be set to a specific speed typically with a tip speed of 15000 fpm. The pin mill may be fitted with two rows of rotor pins and one row of stator pins to give a desired breaking action to the corn kernels. The pin mill may also be equipped with a corrugated liner to aid with the breaking intensity. As the ground material exits the pin mill, it may be subjected to a sifting to separate larger particles from smaller particles. The sifter may be any of the normal gyratory gravity sifters such as the Great Western Model 431, although other reciprocating or turbo type sifters could be used. In one example the ground corn stock can be sifted through a 260 micron screen to obtain a high starch stream that is greater than about 90% starch. The ground stock that flows over the 260 micron screen is directed to downstream processes or to further size reduction processes.

In some embodiments, the separated starch stream (e.g. the high starch stream) may be further processed (on and/or off-site) into sugar and/or one or more bio-chemicals, and the remaining components of the treated stream may be used as feedstock for a corn-to-ethanol fermentation process. For example, the remaining components of the treated stream may be used as feedstock for a dry mill or wet mill corn-to-ethanol fermentation process 207.

Referring again to FIG. 2, the main ground corn stream rather than the whole shelled kernel (as is the case for conventional wet or dry mill corn-to-ethanol fermentation processes) is now the input for the fractionation or whole corn grinding operation 207, which may be, for example, a conventional wet milling operation or a dry milling operation 207a. The output 207b of the fractionation or corn grinding operation 207a can be sent on for further processing 207c (such as fermentation into sugar to produce ethanol or other bio-chemicals).

In some embodiments, the grind rate of the grinding operation 207a is increased relative to a conventional grinding operation in which whole shelled corn is the feedstock, rather than the ground corn stream, to counteract the loss of starch separated into the high purity starch stream. Because increasing the grind rate may also lead to an increased amount of non-starch components, which may take up volume and cut down on production in a fermentation process, in some embodiments, processes according to the disclosure may include additional separation steps to remove non-starch components. For example, the process may utilize the multi-step initial separation process 206a, 206b to remove fiber. In some embodiments, the non-starch components resulting from the increased grind are processed and sold, for example to offset costs of starch removal.

In some such embodiments, the additional separation step 206b removes an amount of fiber to balance the fermentable to non-fermentable ratio back to what it would have been had the high purity stream not been removed. In further such embodiments, up to about 5% of the corn rate, which has a low starch percentage (for example less than about 15% starch on a dry basis), is removed to balance the fermentable to non-fermentable ratio. In some embodiments, increasing the grind rate while balancing the fermentable-to-non-fermentable component ratio will maintain production capacities (e.g. ethanol production) at a level consistent with the original process (i.e. the process using whole corn rather than the ground corn as input to the wet or dry mill corn-to-ethanol fermentation process). In some embodiments, non-starch components resulting from the increased grind rate or are otherwise separated out from the main stream and may be processed and/or sold to offset costs of starch removal.

As a person of skill should be able to understand from reading this disclosure, in some embodiments, the methods and systems according to this disclosure enable production of a quantity of high purity starch stream with limited capital investment as compared to traditional starch producing systems and limited or no loss of downstream production. For example, in some embodiments, the systems include only a limited number of additional pieces of equipment for performing the functions described herein.

A number of embodiments have been described but a person of skill understands that still other embodiments are encompassed by this disclosure. It will be appreciated by those skilled in the art that changes could be made to the embodiments described above without departing from the broad inventive concepts thereof. It is understood, therefore, that this disclosure and the inventive concepts are not limited to the particular embodiments disclosed, but are intended to cover modifications within the spirit and scope of the inventive concepts including as defined in the appended claims. Accordingly, the foregoing description of various embodiments does not necessarily imply exclusion. For example, "some" embodiments or "other" embodiments may include all or part of "some", "other," "further," and "certain" embodiments within the scope of this invention. Methods and devices within the scope of the disclosure can also be defined in accordance with the below embodiments.

Non-inclusive additional embodiments:

1. A process, comprising: processing corn to produce a first high-starch composition comprising soft endosperm and at least about 88% starch on a dry basis and a second feedstock composition comprising hard endosperm suitable for further processing in a corn dry mill or corn wet mill operation.

2. A process according to embodiment 1, wherein processing corn comprises milling the corn to facilitate separation of soft endosperm from hard endosperm, and separating the soft endosperm from hard endosperm resulting in the first high-starch composition comprising soft endosperm and the feedstock composition comprising the hard endosperm.

3. A process according to claim 1 or 2, further comprising producing at least one of ethanol or a bio-based chemical from the feedstock composition in a corn fermentation facility.

4. A process according to any of embodiments 1-3, wherein the feedstock composition further comprises bran and germ.

5. A process according to embodiment 4, wherein the feedstock composition is directed to a fractionation process or a whole corn grinding operation.

6. A process, comprising:
  a. pretreating corn to produce a first stream which facilitates separation of soft endosperm from other components of the corn; and,
  b. separating a second, high-starch stream comprising soft endosperm and at least about 88% starch on a dry basis from the first stream, resulting in a third stream suitable for use as feedstock in dry mill or wet mill corn fermentation processes.

7. A process according to embodiment 6, wherein pretreating comprises milling the corn.

8. A process according to embodiment 7, wherein up to about 50% of the first stream is in high starch form, comprising at least about 88% starch on a dry basis.

9. A process according to embodiment 7, wherein 50% of the first stream is in high starch form.

10. A process according to any of embodiments 6-9, wherein the second stream is substantially free of hard endosperm.

11. A process according to any of embodiments 6-9, wherein the second stream consists essentially of soft endosperm.

12. A process according to any of embodiments 6-11, wherein pretreating results in the soft endosperm having an average particle size sufficiently smaller than the other components of the whole corn to permit separating the soft endosperm from the other components.

13. A process according to embodiment 12, wherein pretreating results in the soft endosperm having an average particle size of about 500 microns or less.

14. A process according any of embodiments 6-13 wherein pretreating comprises milling the corn with a pin mill.

15. A process according to any of embodiments 6-14, further comprising directing the feedstock stream to a wet mill or dry mill ethanol fermentation facility and producing at least one end product from the third, feedstock stream chosen from ethanol and a bio-based chemical.

16. A process according to any of embodiments 6-15, further comprising fractionating the feedstock stream into an endosperm composition, a bran composition and a germ composition.

17. A process according to any of embodiments 6-16, wherein the whole corn is optionally cleaned, optionally tempered, or both prior to pretreating.

18. A process according to any of embodiments 6-17, wherein the high-starch stream has a purity of at least about 90% starch on a dry basis.

19. A process according to embodiment 18, wherein the high-starch stream has a purity level of at least about 94% starch on a dry basis.

20. A process according to embodiment 15, wherein: the third, feedstock stream has a reduced amount of starch as compared to a feedstock stream for which soft endosperm has not been removed; the dry-milling or wet-milling process comprises using a grind rate that is increased relative to a similar corn fermentation process using feedstock for which soft endosperm has not been removed and that at least partially offsets reduction in end product as a result of the reduced amount of starch.

21. A process according to embodiment 20, further comprising removing at least a portion of additional non-starch components produced as a result of the increased grind rate.

22. A corn-to-ethanol fermentation system, comprising:
  a. a dry mill or wet mill ethanol fermentation system which produces beer from feedstock sugars derived from a hard endosperm stream; and,
  b. a bolt-on pretreatment system configured to produce the hard endosperm stream and a high purity starch stream derived from soft endosperm, wherein the high purity starch stream comprises at least about 90% starch on a dry weight basis.

What is claimed is:

1. A process for producing starch streams in a dry mill ethanol fermentation facility, the process comprising:
  (a) dry milling corn grain to produce a milled stream, wherein the milled stream comprises starch, fiber and germ;
  (b) downstream from dry milling, separating starch into a first stream, wherein the separating forms a second stream comprising fiber, germ and starch;
  (c) providing the first stream to a non-ethanol process, wherein the non-ethanol process comprises producing one or more non-ethanol bio-products from starch in the first stream; and
  (d) exposing at least a portion of the starch, the fiber, and the germ from the second stream to fermentation conditions to produce ethanol from starch.

2. The process of claim 1, further comprising:
  (a) saccharifying starch in the second stream into sugar; and
  (b) fermenting sugar in the second stream into ethanol.

3. The process of claim 2, wherein saccharifying is performed before fermenting.

4. The process of claim 2, wherein saccharifying and fermenting are performed simultaneously.

5. The process of claim 2, further comprising processing the second stream through a grinding operation prior to saccharifying starch into sugar.

6. The process of claim 1, further comprising processing starch in the first stream into sugar.

7. The process of claim 6, wherein processing starch in the first stream comprises:
  enzymatically hydrolyzing starch into one or more dextrins; and
  enzymatically hydrolyzing one or more dextrins into one or more sugars.

8. The process of claim 2, further comprising:
  distilling ethanol to form whole stillage;
  separating thin stillage from whole stillage; and
  evaporating water from thin stillage to form syrup.

9. A process according to claim 1, wherein the first stream comprises up to about 50% of the soft endosperm in the corn.

10. A process according to claim 1, wherein dry milling results in at least a portion of soft endosperm having a size of 500 microns or less to facilitate separating the portion of soft endosperm from the corn grain by size.

11. The process of claim 1, wherein dry milling comprises milling corn grain with a pin mill.

12. The process of claim 1, further comprising:
  a) saccharifying starch in the first stream into sugar; and
  b) after saccharifying starch in the first stream, producing one or more non-ethanol bio-products.

13. The process of claim 1, wherein the first stream comprises at least 88% starch on a dry basis.

14. The process of claim 1, wherein the first stream comprises at least 90% starch on a dry basis.

15. The process of claim 1, wherein the first stream comprises at least 94% starch on a dry basis.

16. The process of claim 1, wherein producing one or more non-ethanol bio-products from starch in the first stream comprises refining the first stream to increase purity of starch in the first stream, and wherein the one or more non-ethanol bio-products comprise starch.

17. The process of claim 1, wherein producing one or more non-ethanol bio-products from starch in the first stream comprises providing the first stream to a fermentation process to produce a non-ethanol bio-chemical, wherein the one or more non-ethanol bio-products comprise the bio-chemical.

18. The process of claim 1, wherein the one or more non-ethanol bio-products comprise starch.

19. The process of claim 1, wherein the one or more non-ethanol bio-products comprise one or more non-ethanol bio-chemicals produced via fermentation.

20. The process of claim 1, wherein the one or more non-ethanol bio-products comprise sugar.

* * * * *